United States Patent [19]
Allmaras et al.

[11] Patent Number: 5,922,945
[45] Date of Patent: Jul. 13, 1999

[54] METHOD AND APPARATUS FOR NONINVASIVELY ANALYZING FLOWABLE PRODUCTS

[75] Inventors: Brian J. Allmaras, Forest, Va.; Elwood L. Stokesbury, Westerville; Jianjun Wang, Columbus, both of Ohio

[73] Assignee: Abbott Laboratories, Abbott Park, Ill.

[21] Appl. No.: 08/840,781

[22] Filed: Apr. 16, 1997

[51] Int. Cl.⁶ .......................... G01N 29/02; G01N 29/28
[52] U.S. Cl. .......................... 73/52; 73/61.49; 73/61.79; 73/644; 73/598; 73/600
[58] Field of Search .............................. 73/570, 579, 597, 73/598, 599, 600, 644, 19.03, 52, 61.49, 61.75, 61.79; 702/140, 137, 50; 198/348, 358, 370.01, 370.02

[56] References Cited

U.S. PATENT DOCUMENTS

| | | | |
|---|---|---|---|
| 2,532,507 | 12/1950 | Meunier | 73/600 |
| 3,356,086 | 12/1967 | Behney | 601/2 |
| 3,608,715 | 9/1971 | Snyder et al. | 73/52 |
| 3,760,634 | 9/1973 | Birks | 73/628 |
| 3,877,295 | 4/1975 | Hartman | 73/595 |
| 3,946,599 | 3/1976 | Patt | 73/644 |
| 4,223,790 | 9/1980 | Yoshida | 73/41 |
| 4,428,235 | 1/1984 | Sugiyama | 73/602 |
| 4,466,442 | 8/1984 | Hilmann et al. | 600/431 |
| 4,530,246 | 7/1985 | Pitman et al. | 73/644 |
| 4,726,231 | 2/1988 | Tretout et al. | 73/644 |
| 4,763,525 | 8/1988 | Cobb | 73/599 |
| 4,907,453 | 3/1990 | Marlow et al. | 73/584 |
| 4,914,966 | 4/1990 | White, Jr. et al. | 73/863.01 |
| 5,016,615 | 5/1991 | Driller et al. | 601/2 |
| 5,152,180 | 10/1992 | Waldhauer, Jr. | 73/579 |
| 5,267,985 | 12/1993 | Shimada et al. | 601/2 |
| 5,271,404 | 12/1993 | Corl et al. | 600/454 |
| 5,287,753 | 2/1994 | Routh et al. | 73/861.25 |
| 5,311,781 | 5/1994 | Gates | 73/861.25 |
| 5,333,508 | 8/1994 | Petroff et al. | 73/861.25 |
| 5,369,600 | 11/1994 | Ito et al. | 702/137 |
| 5,370,635 | 12/1994 | Strausak et al. | 604/248 |
| 5,421,211 | 6/1995 | Heckman | 73/861.25 |
| 5,443,071 | 8/1995 | Banjanin et al. | 600/455 |
| 5,487,387 | 1/1996 | Trahey et al. | 600/438 |
| 5,494,038 | 2/1996 | Wang et al. | 73/644 |
| 5,608,164 | 3/1997 | MacLauchlan | 73/599 |
| 5,675,074 | 10/1997 | Melvin, III | 73/52 |

FOREIGN PATENT DOCUMENTS

| | | |
|---|---|---|
| 0139235 | 5/1985 | European Pat. Off. . |
| 0 269 815 | 6/1988 | European Pat. Off. . |
| 37 02 179 | 8/1988 | Germany . |
| 85/00123 | 1/1985 | WIPO . |
| 94/08655 | 4/1994 | WIPO . |

OTHER PUBLICATIONS

Patent Abstracts of Japan, vol. 014 (290) JP 02 092343; Abstract.
Patent Abstracts of Japan, vol. 018 (411), JP 06 122169A; Abstract.

*Primary Examiner*—Michael Brock
*Assistant Examiner*—Rose M. Miller
*Attorney, Agent, or Firm*—Daniel J. Hulseberg; Brian R. Woodworth

[57] ABSTRACT

An apparatus for analyzing a liquid product. The apparatus includes a conveyor assembly having a conveyor belt and an agitator. The conveyor belt is constructed to deliver a unit of liquid product from the agitator to an analysis position. The agitator is constructed to impart motion to a unit of liquid product. The apparatus further includes an ultrasound transmissive pad assembly having a pad defining a chamber therein. A liquid acoustical couplant is contained in the chamber. The ultrasound transmissive pad assembly further includes an ultrasonic transducer in ultrasonic contact with the liquid acoustical couplant. The pad is positioned to contact a unit of liquid product at the analysis position. The pad has an upper portion and a lower portion and is orientated such that the upper portion contacts a unit of liquid product delivered to the analysis position before the lower portion contacts the unit of liquid product delivered to the analysis position.

17 Claims, 3 Drawing Sheets

METHOD AND APPARATUS FOR NONINVASIVELY ANALYZING FLOWABLE PRODUCTS

BACKGROUND OF THE INVENTION

The present invention is directed to a method and an apparatus for analyzing a flowable product. More particularly, the present invention is directed to a method and an apparatus for performing evaluations of product quality using noninvasive techniques.

The use of ultrasonic imaging techniques in the analysis of solid and liquid products is well-known. Ultrasonic waves generated by a transducer are directed into the target product and a receiver is used to receive the ultrasonic waves that are reflected by or transmitted through the target product. The wave pattern received by the receiver can then be analyzed for the purpose of discerning a number of different characteristics of the target product. For example, ultrasonic imaging techniques can be used for the purpose of identifying voids or other physical flaws in solid products. In addition, ultrasonic imaging can be used to detect the presence of particulate matter and air bubbles in liquids. However, the analysis of ultrasound images can be both cumbersome and subjective, thereby resulting in false positive and false negative analyses. In addition, the analysis of ultrasound images can be time-consuming, so thereby significantly increasing the costs associated with this process. For these reasons, it is desirable to have a method and apparatus for performing ultrasound evaluations of products that provide an objective, quick, and reproducible analysis of the flowable product.

SUMMARY OF THE INVENTION

The present invention provides a system and method for conducting ultrasound analysis of flowable products. The system of the present invention includes a conveyor assembly which transports a flowable product to an analysis position. The conveyor assembly includes an agitation assembly constructed to agitate the product so as to create relative movement between the product and its package. The system further includes an ultrasound transmissive pad assembly having an upper end portion and a lower end portion, the pad assembly being positioned so as to be impacted by the product as it is transported by the conveyor assembly. The pad assembly also is positioned such that the upper end portion thereof engages the product prior to engagement of the lower end portion of the pad assembly with the product. The ultrasound transmissive pad assembly includes an ultrasound probe ultrasonically coupled to an ultrasound transmissive pad, the ultrasound probe being constructed to conduct an ultrasonic analysis of the flowable product.

In an alternative embodiment, the present invention includes a conveyor means for transporting a flowable product to an analysis position. The invention further includes an ultrasound transducer assembly positioned to contact a unit of product at the analysis position. The ultrasound transducer assembly has an upper end portion and a lower end portion, the assembly being positioned so as to be impacted by the product at the analysis position. The ultrasound transducer assembly is further positioned such that the upper end portion thereof engages the product prior to engagement of the lower end portion of the assembly with the product. The ultrasound transducer assembly includes an ultrasound probe constructed to conduct an ultrasonic analysis of the flowable product.

BRIEF DESCRIPTION OF THE DRAWING

For a more complete understanding of the present invention, reference may be had to the following Detailed Description read in connection with the accompanying drawings in which.

DETAILED DESCRIPTION

Figure 1:
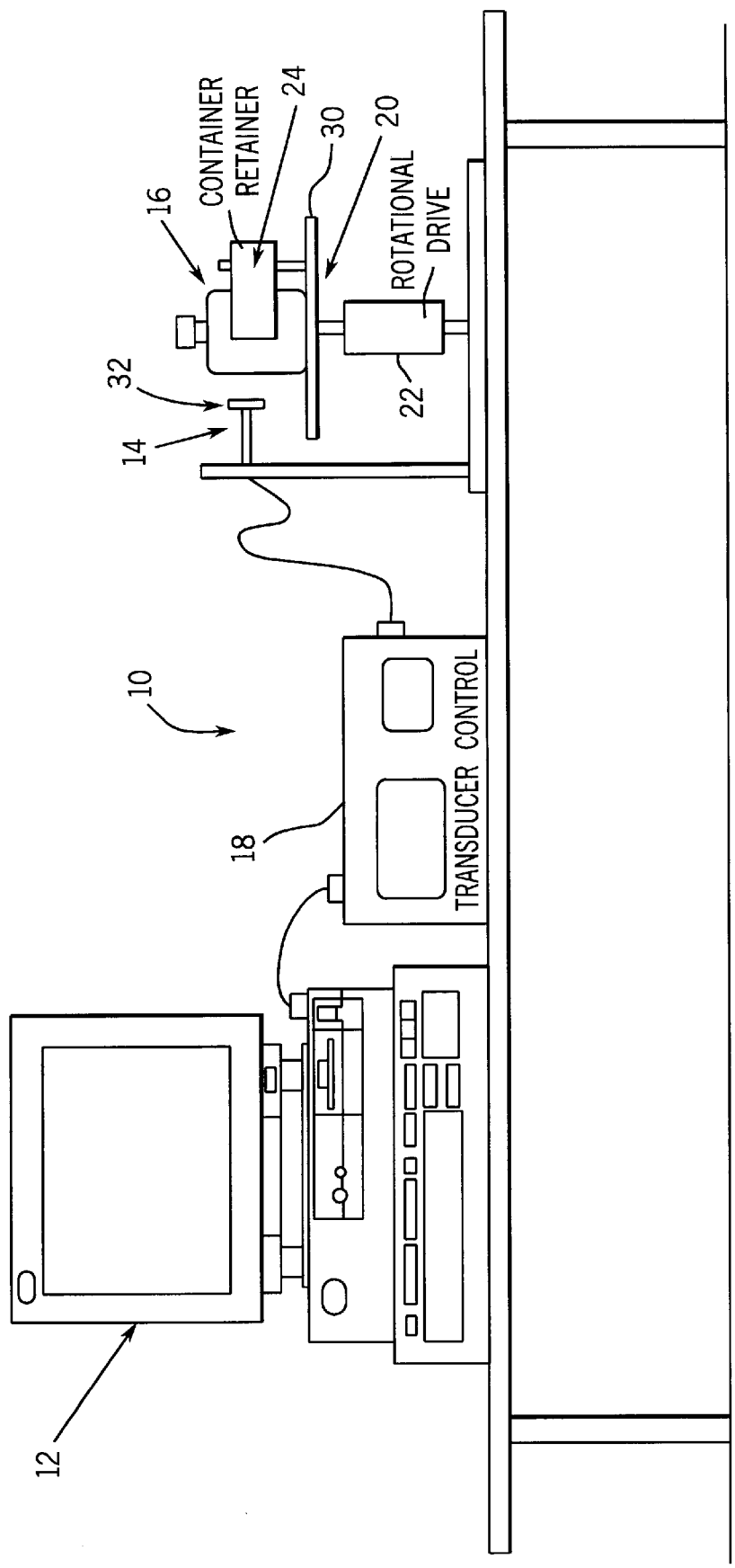
FIG. 1 is a schematic view of a first embodiment of a system constructed in accordance with the present invention.

A system constructed in accordance with the present invention is generally depicted at 10 in FIG. 1. System 10 preferably includes processing unit 12 which is constructed to analyze data collected by system As depicted in FIG. 1, processing unit 12 is a computer system controlled by software and/or hardware, e.g., a computer chip having the requisite programming embedded therein. The function of processing unit 12 will be described in greater detail below. In addition, the functions of system 10 and processing unit 12 are discussed in detail in co-pending U.S. Ser. No. 08/623,721 filed Mar. 29, 1996.

System 10 further includes ultrasonic transducer 14. In the embodiment of the present invention depicted in FIG. 1, ultrasonic transducer 14 both emits and receives ultrasonic waves. For the purposes of this disclosure, system 10 will be referred to as including a single ultrasonic transducer 14 constructed to emit and receive ultrasonic waves. The preferred embodiment of the present invention includes such a transducer 14. However, it will be appreciated that separate ultrasonic transducers 14 can be used for emitting and receiving ultrasonic waves without departing from the scope and spirit of the present invention as claimed in the appended claims. In addition, multiple ultrasonic transducers 14 can be used simultaneously in accordance with the present invention. Finally, ultrasonic transducer(s) 14 utilized in the present invention can be either single or array-type transducers of known construction and operation. In the preferred embodiment of the present invention, ultrasonic transducer 14 also is configured such that ultrasonic waves emitted therefrom are focused using known techniques.

Ultrasonic transducer 14 is mounted such that it can be brought into ultrasonic contact with a packaged, liquid product 16. The term "ultrasonic contact" as used herein refers to a physical relationship wherein ultrasonic waves emitted from ultrasonic transducer 14 are substantially transmitted (i.e., without substantial attenuation) into and received from product 16. As depicted herein, product 16 includes a container constructed of any material known to be permeable to ultrasonic signals, e.g., plastic, glass, metal, and combinations thereof.

Figure 3:
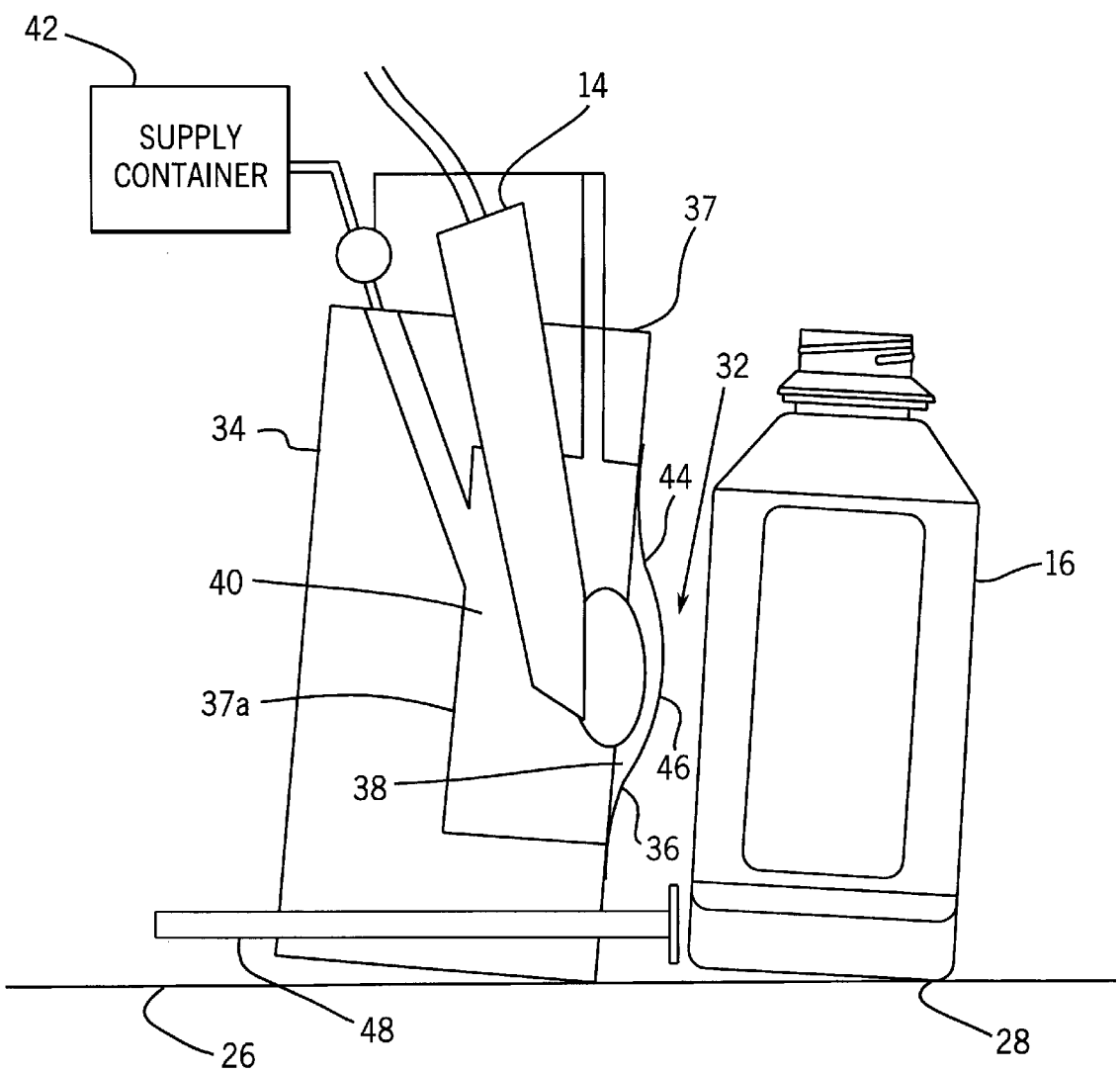
FIG. 3 is a schematic view of an ultrasonic transducer assembly constructed in accordance with the present invention.

Ultrasonic contact can be established between ultrasonic transducer 14 and product 16 by placing an ultrasound coupling gel on an exterior surface of product 16 and placing ultrasonic transducer 14 in contact with the ultrasound coupling gel. Ultrasonic contact also can be established between ultrasonic transducer 14 and product 16 by spraying a liquid, e.g., water, on an exterior surface of product 16, or by immersing product 16 in a liquid, e.g., water, and then bringing ultrasonic transducer 14 into contact with the liquid surrounding the exterior surface of product 16. In the preferred embodiment of the present invention, ultrasonic contact is created between ultrasonic transducer 14 and product 16 using a gel-less technique. Examples of the preferred gelless technique are described in U.S. Pat. No. 5,494,038 to Wang, et al., in co-pending U.S. Ser. No. 08/606,986 filed Feb. 26, 1996 now U.S. Pat. No. 5,770,801 each of which is incorporated herein by reference and each of which are assigned to the assignee of the present invention. A gel-less system 34 employed in the preferred embodiment of the present invention is depicted in FIG. 3.

In a first embodiment disclosed in U.S. Pat. No. 5,494,038, the gel-less technique employs a membrane that defines pores therethrough. The membrane defines a chamber that contains a liquid acoustical couplant such as water. Ultrasonic transducer 14 can be placed in contact with the membrane defining the chamber or can be disposed within the chamber. The pores defined through the membrane are sized such that molecules of the liquid acoustical couplant can become entrained therein or pass therethrough, thereby placing the ultrasonic transducer and the surface of the target object in what will be referred to as indirect contact, i.e., in contact through the liquid acoustical couplant and through the porous membrane. Through the resulting indirect contact between the transducer and the surface of the target object, ultrasonic waves emitted by the ultrasonic transducer are directed into and received from the target object.

In a second embodiment disclosed in U.S. Pat. No. 5,494,038, the gel-less technique employs a membrane defining pores therethrough. The membrane and the wave emitting/receiving end of the ultrasonic transducer define a chamber therebetween. A liquid acoustical couplant, e.g., water, is disposed in the chamber. The pores of the membrane are sized such that molecules of the liquid acoustical couplant can become entrained therein or pass therethrough, thereby placing the surface of the target object in indirect contact with the liquid acoustical couplant in the chamber and with the ultrasonic transducer. It will be appreciated that various modifications can be effected to the gel-less techniques disclosed in U.S. Pat. No. 5,494,038 without departing from the scope of the present invention.

A transducer control system 18 of known construction and operation can be coupled via an electrical connection or cable to ultrasonic transducer 14. In those embodiments in which transducer control system 18 is used, system 18 also preferably is coupled via an electrical connection or cable to processing unit 12. Transducer control system 18 controls the operating parameters, e.g., frequency, amplitude, and dynamic focusing, of ultrasonic transducer 14 by directing control signals to transducer 14. Ultrasonic waves received by ultrasonic transducer 14 are transferred through an electrical connection or cable to transducer control system 18, such transfer occurring directly or occurring after ultrasonic transducer 14 converts the received wave signal to a form interpretable by transducer control system 12. Transducer control system 18 then converts the received ultrasonic wave pattern into a wave image signal that is readable by processing unit 12 and transfers the resulting wave image signal to processing unit 12. Transducer control system 18 preferably can be adjusted by an operator to provide the desired ultrasonic wave parameters and to provide the desired wave image to processing unit 12. It will be appreciated that the functions of processing unit 12, transducer control system 18, and ultrasonic transducer 14 can be combined into a single unit having each of these components' respective functions.

In the embodiment of the present invention depicted in FIG. 1, system 10 is configured to be mounted on table, platform, floor, or other surface. In the depicted embodiment, a platform 20 is provided to support product 16 thereon. Platform 20 can be configured for rotation. In those embodiments of the present invention in which platform 20 can be rotated, such rotation can be effected manually or by the selective operation of a rotational drive system 22 of known construction. Container retainer 24 is mounted on platform 20 and is configured to releasably retain product 16 on platform 20 in order to prevent movement of product 16 relative to platform 20. Ultrasonic transducer 14 and platform 20 are constructed such that ultrasonic transducer 14 can be placed in ultrasonic contact with product 16. In the embodiment of the present invention depicted in FIG. 1, platform 20 is slidable such that it can be moved to place ultrasonic transducer 14 in ultrasonic contact with product 16. In this embodiment, drive system 22 can be configured to impart linear movement and rotational movement to platform 20. In an alternative configuration of the embodiment depicted in FIG. 1, ultrasonic transducer 14 is mounted such that it can be moved toward and into ultrasonic contact with product 16 while platform 20 is constructed to impart rotational movement to product 16.

Platform 20 and rotational drive system 22 constitute one embodiment of a conveyor means in accordance with the scope of the present invention. Platform 20, rotational drive system 22, and a mechanism for imparting linear movement to ultrasonic transducer 14 constitute a second embodiment of a conveyor means in accordance with the present invention. As used herein, the term "conveyor means" is intended to encompass any combination of known systems and mechanisms for imparting agitation to product 16 and for imparting relative movement between ultrasonic transducer 14 and product 16 such that product 16 is placed in direct of indirect contact with transducer 14. For example, robotics can be provided to impart the requisite relative motion between transducer 14 and product 16 and the requisite agitation of product 16.

Figure 2:
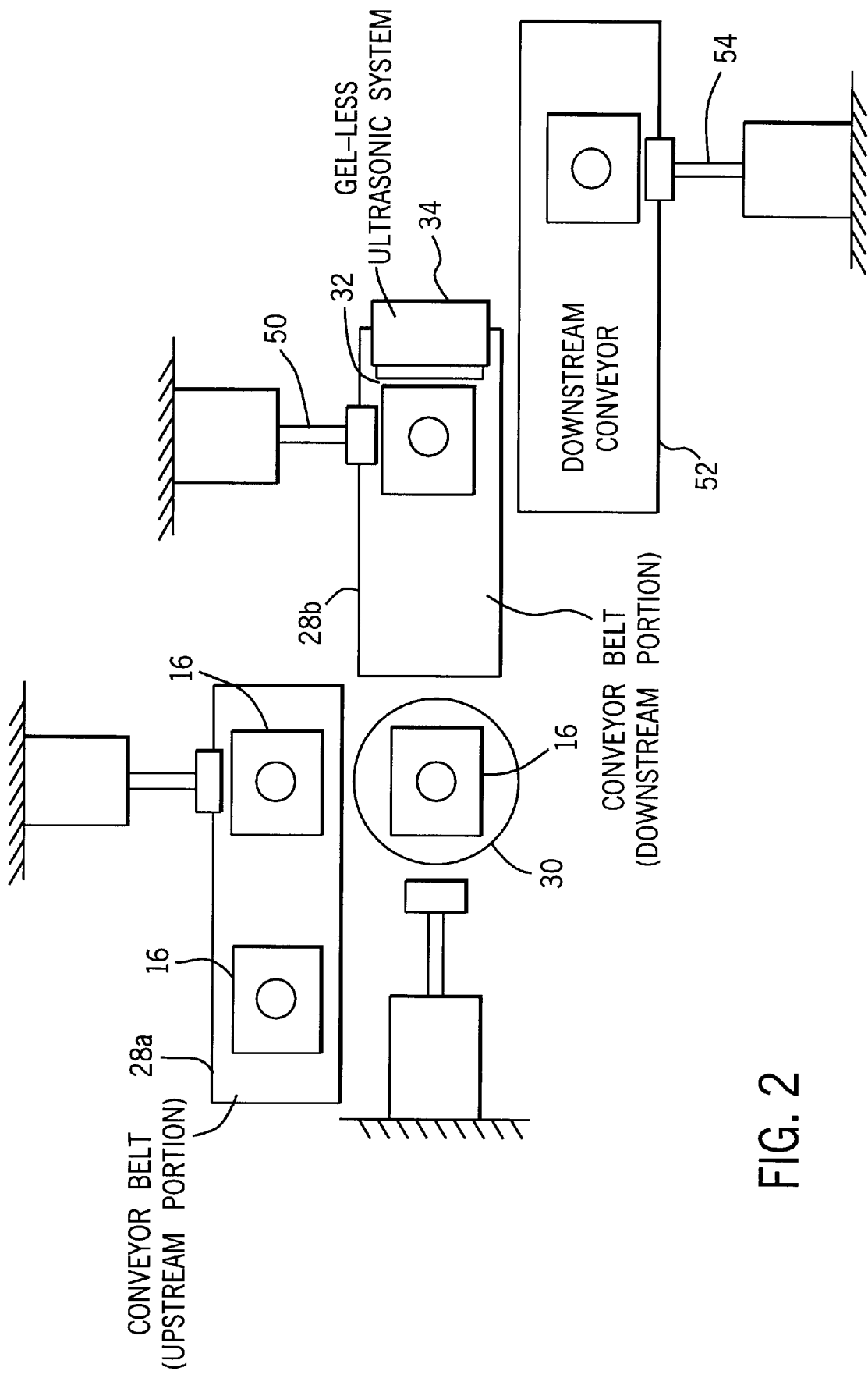
FIG. 2 is a schematic view of a second embodiment of a system constructed in accordance with the present invention.

FIG. 2 depicts an alternative embodiment of a conveyor means constructed in accordance with the present invention. In the embodiment of the present invention depicted in FIG. 2, system 10 is configured to be part of a system in which a plurality of products 16 are conveyed along a predetermined path, for example, an assembly line. In this embodiment, conveyor assembly 26 including conveyor belt 28 is provided to move products 16 towards ultrasonic transducer 14. Conveyor belt 28 can be of any known construction. As depicted in FIG. 2, conveyor belt 28 is substantially horizontal and is positioned beneath product 16. It will be appreciated that conveyor belt 28 also can configured to impart movement to product 16 if one or two conveyor belts are positioned substantially vertically so as to contact one or more sides of product 16. Alternatively, conveyor belt 28 can be replaced with other known mechanisms for the transportation of products including, but not limited to, star wheels.

In the embodiment depicted in FIG. 2, conveyor assembly 26 includes agitator 30 which preferably is constructed to impart rotational movement to product 16. The importance of imparting movement to product 16 will be discussed in detail below. Agitator 30 also can be configured to impart other types of agitation to product 16. For example, agitator 30 can be configured to impart vibratory energy to product 16 so as to create random movement of particles and air bubbles within product 16. Alternatively, agitator 30 can be configured to impart motion to product 16 in any desired plane. The preferred embodiment of the present invention includes an agitator 30 which imparts rotational motion to product 16 as it is transported by conveyor assembly 26. Agitator 30 preferably is oriented and constructed to impart substantially planar movement to particles and air bubbles within product 16. In the preferred embodiment, agitator 30 is a turntable which rotates product 16 about a longitudinal axis of the container in which product 16 is contained. In the preferred embodiment, additional elements of known construction are provided to deliver product 16 to agitator 30 from an upstream portion 28a of conveyor belt 28 and to deliver product 16 to a downstream portion 28b of conveyor belt 28 from agitator 30. In addition, a product retention element of known construction can be provided to prevent product 16 from moving relative to agitator 30 as it is being rotated.

In another alternative embodiment of the present invention not depicted in the accompanying figures, a conveyor means including robotics is provided. The robotics can be constructed to impart relative movement between ultrasonic transducer 14 and product 16 such that ultrasonic transducer 14 and product 16 are brought into contact with one another. The robotics also can be constructed to impart agitation, e.g., rotational movement, to product 16 prior to the time that product 16 is brought into contact with ultrasonic transducer 14. Finally, such robotics can include ultrasonic transducer 14. That is, ultrasonic transducer 14 can be incorporated into the robotics such that ultrasonic transducer 14 is in ultrasonic contact with product 16 as the robotics conveys and/or agitates product 16. The terms "conveyor means" and "conveyor assembly" are intended to include systems utilizing robotics of this type.

While in analysis position 32, product 16 is in ultrasonic contact with ultrasonic transducer 14. As above-discussed, ultrasonic contact between ultrasonic transducer 14 and product 16 can be effected by conveyor assembly 26 by moving ultrasonic transducer 14 into contact with product 16 or by moving product 16 into contact with ultrasonic transducer 14. In the preferred embodiment of the present invention depicted in FIG. 2, product 16 is moved into ultrasonic contact with ultrasonic transducer 14 by upstream portion 28a and downstream portion 28b of conveyor belt 28 of conveyor assembly 26.

It will be appreciated that other configurations of the embodiment of the present invention depicted in FIG. 2. are possible. For example, ultrasonic transducer 14 can be mounted on a rotatable head such that ultrasonic transducer 14 is brought into ultrasonic contact with product 16 as product 16 is moved past analysis position 32 by conveyor belt 28. In addition, ultrasonic transducer 14 can be mounted on a reciprocating mechanism whereby it can be moved into and out of ultrasonic contact with product 16 as product 16 is carried by conveyor assembly 26.

In the preferred embodiment of the present invention, transducer 14 is placed in ultrasonic contact with product 16 through the use of a gel-less system 34 such as that depicted in FIG. 3. The gel-less system includes pad 36 and block 37 which define chamber 38 therebetween. Pad 36 is preferably constructed of a porous material as above-discussed. Block 37 preferably is constructed of stainless steel and defines a recess 37a therein. In the preferred embodiment of the present invention, recess 37a has a substantially rectangular cross-section. However, it will be appreciated that other cross-sectional configurations of recess 37a are possible without departing from the scope of the present invention as claimed in the appended claims. As depicted in FIG. 3, pad 36 is disposed over recess 37a in block 37. Pad 36 preferably is fluidly sealed to block 37 about the periphery of recess 37a using known techniques such that liquid within chamber 38 does not pass through the junction between block 37 and pad 36.

A liquid acoustical couplant 40 such as isoproponal alcohol is retained in chamber 38. Couplant 40 preferably has a molecule size that is equal to or less than the size of the pores defined by the porous material of pad 36. In this way, couplant 40 will pass through or become entrapped in the pores of pad 36, thereby providing ultrasonic contact between the interior of chamber 38 and an object in contact with an exterior surface of pad 36. As depicted in FIG. 3, the presence of liquid acoustical couplant 40 will cause pad 36 to distend outwardly from recess 37a.

In the preferred embodiment of the present invention, chamber 38 is fluidly connected to a supply container 42 containing a reserve supply of couplant 40. A system of known construction, e.g., a regulated valve system, can be provided to ensure that the volume of couplant 40 contained in chamber 38 is maintained at or above a minimum level during use of system 10.

Ultrasound transducer 14 is positioned within chamber 38 as depicted in FIG. 3. In the preferred embodiment, ultrasound transducer 14 is positioned such that it extends slightly beyond block 37. In one embodiment of the present invention, ultrasonic transducer 14 is positioned such that its forward end extends approximately 4–5 mm beyond block 37.

It will be appreciated that a force is created at the point of contact between conveyor belt 28 and product 16, thereby allowing conveyor belt 28 to carry product 16 to analysis position 32. An equal and oppositely directed force is applied by pad 36 to product 16 when contact is made therebetween, thereby preventing further downstream movement of product 16 when it is in analysis position 32.

In the preferred embodiment of the present invention, pad 36 has an upper portion 44 and a lower portion 46. Pad 36 is oriented such that upper portion 44 contacts product 16 before lower portion 46 contacts product 16. For example, if conveyor assembly 26 is constructed to deliver product 16 to analysis position 32 along a substantially horizontal path, and if product 16 presents a substantially vertical surface to pad 36 for analysis, pad 36 preferably will be oriented such that upper portion 44 is tilted forward relative to lower portion 46, thereby causing product 16 to contact upper portion 44 before contacting lower portion 46.

Due to the difference in the elevations at which conveyor belt 28 and pad 36 contact product 16, a torque force is created on product 16. This torque force causes a slight rotation or turning of product 16. Rotation or turning of product 16 stops when this torque force is offset by the weight of product 16. It will be appreciated that the weight of product 16 creates a vertical, downward force due to gravity and that it is this force that offsets the torque force. As a result, product 16 is in a stable, balanced position when it is at analysis position 32. Ultrasonic transducer 14 preferably is disposed within chamber 38 such that it is substantially normal to the surface of product 16 in analysis position 32. The accuracy of the ultrasound testing conducted by system 10 of the present invention is enhanced by the relative stability of product 16 when it is in analysis position 32.

System 10 of the present invention mimics a manual test operation and does not cause significant vibration of product 16, thus enhancing the accuracy of the ultrasound analysis performed thereby. As product 16 comes into contact with upper portion 44 of pad 36, upper portion 44 provides a cushioning of the impact therebetween due to the fact that pad 36 contains liquid acoustical couplant 40. That is, due to the relative flexibility of pad 36 and the relative mobility of liquid acoustical couplant 40 contained therein, the initial impact between upper portion 44 and product 16 and the subsequent angular movement of product 16 relative to conveyor belt 28 impart relatively little vibration to product 16. In other words, the impact between product 16 and pad 36 is made relatively smooth by the relative orientation and configuration of gel-less system 34. This aspect of the present invention is particularly useful when system 10 is used to inspect low viscosity products which are susceptible to agitation from even slight vibrational energies.

It will be appreciated that modifications of the relative orientations of gel-less system 34 and product 16 may be necessary in those cases in which the container in which product 16 is contained does not present a substantially vertical face to gel-less system 34 for ultrasonic analysis or in those cases in which conveyor assembly 26 does not deliver product 16 to analysis position 32 along substantially horizontal path.

The preferred angular orientation of gel-less system 34 relative to the direction of travel of product 16 as it reaches analysis position 32 will be dependent upon a variety of factors, including the speed at which product 16 is delivered to analysis position 32, the magnitude of the frictional force between product 16 and conveyor belt 28, the shape of product 16, the size of product 16, and other physical properties of product 16. Therefore, it is necessary to determine the preferred angular orientation of gel-less system 34 for each product being tested using system 10 of the present invention.

System 10 preferably includes a first piston 48 which, when activated, urges product 16 away from pad 36, that is, in a direction substantially opposite to the direction in which product 16 is delivered to analysis position 32 by conveyor assembly 26. Second piston 50 is also provided. When activated, second piston 50 moves product 16 off of conveyor assembly 26 and away from analysis position 32, thereby permitting the inspection of a subsequent unit of product 16. In the preferred embodiment of the present invention, second piston 50 moves product 16 away from analysis position 32 in a direction that is substantially perpendicular to the direction in which product 16 is delivered to analysis position 32 by conveyor assembly 26 and substantially perpendicular to the direction of motion imparted by first piston 48. It will be appreciated that the removal of product 16 from conveyor assembly 26 may cause harm to pad 36 if product 16 is in contact with pad 36 as it is moved. For this reason, first piston 48 is provided to move product 16 away from pad 36 before second piston 50 is activated. The relative timing of the activations of first piston 48 and second piston 50 is preferably controlled such that second piston 50 moves product 16 off of conveyor assembly 26 after first piston 48 has moved product 16 away from pad 36 and before conveyor belt 28 causes product 16 to be moved back into engagement with pad 36.

Upon removal of product 16 from analysis position 32, pad 36 and liquid acoustical couplant 40 contained therein will return to their rest positions until contacted by another unit of product 16. In the event that liquid acoustical couplant 40 is released from chamber 38 within pad 36, additional couplant 40 is supplied to chamber 38 from supply container 42. It has been found that the release of couplant 40 through the pores of pad 36 can be beneficial in that it tends to clean the surface of pad 36. Further, the refilling of the pores in pad 36 enhances the capillary action in these pores, thereby enhancing the ultrasonic signal transmission between transducer 14 and product 16.

A downstream conveyor system 52 is provided to carry product 16 to subsequent processing or packaging stations after it has been moved off of conveyor belt 28 by second piston 50.

In the preferred embodiment of the present invention, a rejection piston mechanism 54 is provided. Rejection piston mechanism 54 is constructed to remove unacceptable units of product 16 from downstream conveyor system 52. Rejection piston mechanism 54 preferably is controlled by processing unit 12 such that it is activated when processing unit 12 determines that the quality of product 16 is not within acceptable parameters. As discussed herein, processing unit 12 produces a "rejection signal" when the quality of product 16 is not within acceptable parameters, such signal activating rejection piston mechanism 54.

It is to be appreciated that pistons 48 and 50, downstream conveyor system 52, and rejection piston mechanism 54 can be replaced by robotics without departing from the intended spirit and scope of the present invention.

System 10 is configured for the ultrasonic testing of one or more units of product 16. System 10 provides a capacity for the static or dynamic ultrasonic analysis of product 16. Static testing can be used to provide a variety of information regarding solid products, flowable products, or products that have both solid and flowable components. Dynamic testing can be used to provide a variety of information regarding flowable products or products that have both solid and flowable components. Dynamic testing can be used with solid products solely for the purpose of confirming that the product is solid or identifying empty containers.

In a static testing procedure, product 16 is not agitated. Thus, when system 10 is operated in a static testing mode, conveyor assembly 26 does not rotate or otherwise agitate product 16. When system 10 is operated in the preferred, dynamic testing mode, conveyor assembly 26 agitates product 16 as above-discussed. It will be appreciated that agitator 30 of the preferred embodiment of the invention can be configured to rotate any number of degrees, provided that the rotation is sufficient to impart movement to product 16. In addition, the speed profile, i.e., speed and acceleration, at which agitator 30 agitates product 16 can be varied dependent upon the nature of the product 16 and the operating parameters of processing unit 12, transducer control system 18, and ultrasonic transducer 14.

Static testing can be used to provide a variety of information regarding product 16, including the detection of air bubbles, foreign substances, or structural flaws in product 16. Static testing can be used to analyze product 16 for the purposes of determining whether the container carrying product 16 has been underfilled or overfilled. Static testing also can be used to analyze the overall consistency of product 16.

Dynamic testing can be employed to provide all of the information provided with static testing. In addition, dynamic testing can be used to analyze the flow characteristics of product 16 following agitation thereof Due to changes that occur to some products 16 when they are tainted or spoiled, the flow characteristics of product 16 can be used to identify spoiled or tainted product. For example, milk products tend to become more viscous when they are spoiled. Accordingly, it is possible to determine whether a milk product is spoiled by analyzing the flow characteristics of the milk product using a dynamic testing technique in accordance with the present invention.

In a static testing procedure conducted in accordance with the present invention, product 16 is placed in ultrasonic contact with ultrasonic transducer 14. Ultrasonic waves from ultrasonic transducer 14 are directed into product 16. In those embodiments of the present invention in which ultrasonic transducer 14 is configured to emit and receive ultrasonic waves, ultrasonic transducer 14 also will receive a wave pattern from product 16 which has been altered as a result of reflections and deflections of the emitted ultrasonic wave caused by the reflective components of product 16. It is well-known in the art that the various reflective components of an object, e.g., air bubbles and particulates, will cause reflections/defections of an ultrasonic wave, thereby enabling the creation of an ultrasonic image of the object. As above-discussed with respect to the apparatus of the present invention, ultrasonic transducer 14 and/or processing unit 12, processes the received ultrasonic wave pattern and transforms it into a form that is readable by system 10.

Processing unit 12 analyzes the transformed wave image on a pixelby-pixel basis and assigns a numerical gray scale value to each pixel. As used herein, the term "pixel" refers to a finite region within the wave image. The pixels can have a variety of geometric configurations and dimensions, although in common practice the pixels typically will be rectangular or square. The number of pixels used will be determined by the capacity of processing unit 12 and the characteristics of product 16 undergoing analysis. In one embodiment of the present invention, processing unit 12 analyzes the transformed wave image using 22,000 pixels arranged in a 220×100 configuration. One of ordinary skill in the art will appreciate that other pixel arrangements are possible without departing from the spirit and scope of the present invention.

The magnitude of the gray scale value assigned to each pixel is determined by the intensity of the signal in each pixel. A mean gray scale value for the wave image can be calculated by summing each assigned gray scale value and dividing the sum by the number of pixels. The mean gray scale value for the wave image will be higher than an acceptable mean gray scale value where the number of particulates, coagulations, foreign objects, and/or air bubbles (i.e., reflective components) in product 16 is higher than acceptable. Thus, an acceptable range of mean gray scale values for product 16 can be established by analyzing units of product 16 that have been previously deemed acceptable using known testing techniques, e.g., microbiological, physical, chemical, and visual testing, and combinations thereof. Processing unit 12 can then compare the calculated mean gray scale value to the acceptable range of mean gray scale values for product 16 in order to determine whether the unit of product 16 undergoing analysis is acceptable. In the event that the calculated mean gray scale value is not within the acceptable range, processing unit 12 preferably generates a rejection signal indicating that the unit of product should be discarded.

Static testing also can be used for the purpose of identifying foreign objects in product 16. Upon the assignment of gray scale values for each pixel of the wave image, processing unit 12 will analyze the assigned values for the purpose of identifying large gray scale value deviations from one pixel to the next. Unlike air bubbles and coagulations, foreign objects will tend to produce higher intensity images and therefore will have a higher gray scale value. Thus, the occurrence of a significant variation in gray scale value from pixel-to-pixel will tend to indicate the presence of a foreign object in product 16. In this static testing mode, processing unit will compare the variations of gray scale values of the wave image to an acceptable range of variations to determine whether product 16 contains an unacceptable foreign object. Here again, the acceptable range of variations of gray scale values can be determined by testing units of product 16 that have been proven to be acceptable using other techniques. It will be appreciated that the gray scale deviation standard employed by processing unit 12 to identify the presence of a foreign object in product 16 will vary dependent upon the nature of product 16. In the event that processing unit 12 detects an unacceptable foreign object in product 16, processing unit 12 will generate a rejection signal as above-discussed.

Static testing also can be used to indicate the fill level of product 16. Due to the nearly infinite resistance of air to ultrasonic waves, there will be a discontinuation in the wave image at the interface between product 16 and air within the container containing product 16. Processing unit 12 can identify this interface by analyzing the gray scale values of the wave image for the purpose of establishing the air/product interface. Upon identifying the location of the interface, processing unit 12 compares the fill level of product 16 to an acceptable range of fill levels to determine whether product 16 is overfilled or underfilled. In the event that the interface location does not fall within a preselected acceptable range of fill levels, processing unit 12 will generate a rejection signal as above-discussed. It will be appreciated that the positioning of ultrasonic transducer 14 relative to product 16 must be controlled in order to provide accurate fill information. System 10 of the present invention preferably is configured to provide a fixed or standard relationship between ultrasonic transducer 14 and product 16 when product 16 is undergoing analysis.

Dynamic testing differs from static testing in that two or more wave images received by processing unit 12 are analyzed in order to determine certain characteristics of product 16. As above-discussed, each of the analyses that can be performed using static testing can be conducted by analyzing a single image of a dynamic test, that is, any one of a plurality of images. However, rather than analyzing a static product, these tests analyze a snapshot of a dynamic product, i.e., a product in motion. Product 16 is set in motion by an agitator or comparable device described herein. As above-discussed with respect to the preferred embodiment of the apparatus of the present invention, a variety of known types of agitators can be used to impart different types of motion to product 16. For the purposes of this disclosure, the motion imparted by the agitator will be a rotational motion. However, it will be appreciated that the dynamic testing techniques described herein apply to all motions that can be imparted to product 16 by agitator 30.

In a dynamic testing procedure conducted in accordance with the method of the present invention, a flowable product 16 is set in motion by agitator 30. Ultrasonic transducer 14 is then brought into ultrasonic contact with product 16 via pad 36 as above-discussed. Ultrasonic transducer 14 emits a plurality of ultrasonic waves which enter product 16 and are then received by ultrasonic transducer 14. Ultrasonic transducer 14 preferably transforms the received wave images into a form that is readable by processing unit 12 and the transformed wave images are transmitted to processing unit 12 for analysis.

In accordance with the present invention, processing unit 12 assigns gray scale values on a pixel-by-pixel basis to a first of the plurality of wave images received by processing unit 12 from ultrasonic transducer 14, thereby establishing a reference for further analysis of product 16. In accordance with the preferred embodiment of the present invention, processing unit 12 analyzes the gray scale values assigned to each pixel for the purpose of identifying those pixels that have a threshold value. Pixels having a gray scale value higher than the predetermined threshold value reflect the presence of air bubbles, particulates, foreign objects, or coagulants in product 16. For the purposes of this disclosure, air bubbles, particulates, foreign objects, and coagulants will be referred to as "reflective contents" of product 16. The threshold value used by processing unit 12 to identify reflective contents will vary dependent upon the product undergoing analysis and the purpose of the test. The threshold value preferably is preprogrammed into processing unit 12.

In analyzing the assigned gray scale values, processing unit 12 analyzes a neighborhood around each pixel having a gray scale value at least as great as the threshold value for the purpose of identifying the periphery of each reflective content represented by a reflective image. Processing unit 12 establishes the periphery of each reflective image by identifying pixels in the neighborhood that do not have a gray scale value at least as large as the threshold value. Processing unit 12 then calculates the center or mass center of each of the reflective images based upon the identified periphery thereof. In the preferred embodiment, processing unit 12 calculates the mass center of each of the reflective images based upon the identified periphery thereof and the individual pixel gray scale values. Use of mass center in this analysis is advantageous in that it enables processing unit 12 to better identify individual reflective contents moving through product 16. In one embodiment of the present invention, processing unit 12 is configured such that it will generate a rejection signal in the event that the dimensions of the reflective image are larger than a predetermined threshold value, thereby indicating the presence of a foreign object or an undesirable coagulation or agglomeration. It will be appreciated that this portion of the dynamic analysis of product 16 can also be conducted on a static basis.

Processing unit 12 subsequently conducts the same analyses of a second of the plurality of received wave images for the purpose of identifying the center or mass center of each of the reflective images of the reflective contents of product 16 in the subsequent image. It is preferred that the second wave image analyzed by processing unit 12 reflects a "snapshot" of product 16 at a time sufficiently subsequent to the time of the first wave image such that the reflective contents of product 16 have been given adequate time to move. The desired time delay between the first and second analyzed wave images will vary based upon the degree of agitation imparted to product 16 and based upon the viscosity of product 16. If a high degree of agitation is imparted to product 16, or if product 16 has a relatively low viscosity, it is preferable that the first and second analyzed wave images be relatively close in time. If a relatively low degree of agitation is imparted to product 16, or if product 16 has a relatively high viscosity, it is preferable that the first and second analyzed wave images be farther apart in time.

Vectors can be established to represent the movement of the centers or mass centers of each reflective image from the first analyzed wave image to the second analyzed wave image. By assigning x and y axis values to each position of each reflective image in each analyzed wave image, the displacement of the center or mass center of each reflective image, and thus the magnitude of each vector, can be established using the Pythagorean theorem. The velocity of each reflective content of product 16 can be calculated by dividing the displacement of the center of each reflective image by the amount of time that elapsed between the first and second analyzed wave images.

In the preferred embodiment of the present invention, vectors are established by processing unit 12 by analyzing more than two separate wave images. For example, processing unit 12 can analyze four separate wave images in order to establish vectors.

As above-discussed, in the preferred embodiment of the present invention, the mass center x, y coordinates of the reflective contents of the first and last images will be used to calculate the vector. In those cases in which more than two wave images are analyzed, the analyzed wave images can be relatively close in time to one another, thereby providing greater assurances that processing unit 12 is properly tracking reflective contents and creating vectors for each reflective content. In one embodiment of the present invention, processing unit 12 is configured such that it confirms that a single reflective content is being tracked by confirming that the mass of the reflective content, as determined by the sum of the pixel gray scale values for the image of the reflective content, is substantially constant from frame-to-frame. Nevertheless, vectors can be established using any two or more separate wave images taken at separate times without departing from the scope of the present invention. All intermediate images and coordinate values are used only for continuous tracking purposes.

Processing unit 12 performs a statistical analysis of vectors for the purpose of calculating a mean displacement or a mean velocity for the reflective contents of product 16. As above-noted, the velocity of each reflective content of product 16 is proportional to the displacement of each reflective content of product 16. Therefore, either the displacement or the velocity of each reflective content of product 16 can be used in performing the statistical analysis. The processing unit 12 then compares the calculated mean displacement or mean velocity to an acceptable range of displacements or velocities for reflective contents of product 16. In addition, processing unit 12 determines a statistical skewness for the displacements or velocities of the reflective contents of product 16. The resulting skewness also is compared to an acceptable range of skewness for the displacements or velocities of reflective contents of product 16. In the event that the mean displacement, the mean velocity, or the skewness is not within the acceptable range, processing unit 12 generates a rejection signal indicating that product 16 is not acceptable. As above-discussed, processing unit 12 activates rejection piston 54 when processing unit 12 generates a rejection signal for the purpose of discarding unacceptable product 16.

It will be appreciated that other statistical analyses can be conducted using dynamic testing techniques. For example, processing unit 12 can be configured such that it analyzes the coordinates of each vector for the purpose of determining whether the reflective contents of product 16 are moving at substantially the same rate in all areas of the reflected image. In the event that reflective contents in certain areas of the reflected image are moving at rates substantially different than the remainder of product 16, or in the event that reflective contents in certain areas of the reflected wave image are moving in substantially different directions than the remainder of product 16, it is likely that product 16 is undergoing localized changes, e.g., localized spoilage or localized coagulation. Processing unit 12 preferably generates a rejection signal in the event that the flow rates or directions of reflective contents in a certain area of the reflected wave image are substantially different than the flow rates or directions of reflective contents in the remainder of the reflected image. In addition, processing unit 12 can be configured such that it analyzes the head and tail coordinates for each vector for the purpose of determining whether they are evenly distributed through the reflected wave image. In the event that product 16 is undergoing localized changes in characteristics, e.g., viscosity, there may be certain areas of the reflected wave image through which no vector passes. If processing unit 12 detects an inconsistency in the distribution of coordinates of the established vectors, it generates a rejection signal.

Acceptable ranges for mean displacement, mean velocity, and skewness are calculated on a product-by-product basis due to variations in product viscosity and particulate content. In addition, acceptable ranges for these parameters must be determined based upon the speed at which product 16 is agitated and the length of time that is allowed to lapse between the agitation of product 16 and the ultrasonic testing of product 16. For this reason, acceptable ranges are preferably established by conducting dynamic testing in the above-discussed manner on products 16 that have been determined to be acceptable using known testing methods such as chemical and visual testing. The acceptable ranges for these parameters are preferably established using the same rate of agitation and the same time delay between agitation and ultrasonic testing that will be used in the actual testing procedure.

It is to be appreciated that the operation of processing unit 12 for particle tracking can be conducted using fuzzy logic similar to the approach disclosed in "Fuzzy Logic Particle Tracking Velocimetry" by Mark P. Wernet, prepared for the Optical Diagnosis in Fluid and Thermal Flow sponsored by the Society of Photo-Optical Instrumentation Engineers, San Diego, Calif. Jul. 11–16, 1993.

Although the apparatus and method of the present invention have been described in detail herein with respect to certain preferred embodiments, it will be apparent to one of ordinary skill in the art that various modifications to the present invention without departing from the intended spirit and scope of the invention as claimed in the appended claims.

What is claimed is:

1. An apparatus for analyzing a flowable product, said apparatus comprising:
    a conveyor assembly comprising a conveyor belt and an agitator, said conveyor belt constructed to deliver a container containing flowable product from said agitator to an analysis position, said agitator constructed to impart motion to a flowable product within a container;
    an ultrasound transmissive pad assembly defining a chamber therein, a liquid acoustical couplant contained in said chamber, said ultrasound transmissive pad assembly further comprising an ultrasonic transducer in ultrasonic contact with said liquid acoustical couplant, said ultrasound transmissive pad assembly positioned to contact a container containing flowable product in said analysis position, said ultrasound transmissive pad assembly having an upper portion and a lower portion, said ultrasound transmissive pad assembly orientated such that said upper portion contacts a container containing flowable product delivered to said analysis position by said conveyor assembly before said lower portion contacts the container containing flowable product delivered to said analysis position by said conveyor assembly.

2. An apparatus for analyzing a flowable product in accordance with claim 1, wherein said conveyor belt delivers a container containing flowable product from said agitator to said analysis position in a first direction, said apparatus further comprising a first piston positioned proximal said analysis position, said first piston constructed to move a container containing flowable product in said analysis position in a second direction, said second direction being opposite said first direction, said first piston constructed to move a container containing flowable product to a position spaced from said ultrasound transmissive pad assembly.

3. An apparatus for analyzing a flowable product in accordance with claim 1, wherein said apparatus further comprises a second piston positioned proximal said analysis position, said second piston constructed to move a container containing flowable product off of said conveyor belt.

4. An apparatus for analyzing a flowable product, said apparatus comprising:
    a conveyor means for delivering a container containing flowable product to an analysis position;
    an ultrasound transducer assembly positioned to contact a container containing flowable product at said analysis position, said ultrasound transducer assembly having an upper portion and a lower portion, said ultrasound transducer assembly orientated such that said upper portion contacts a container containing flowable product delivered to said analysis position by said conveyor means before said lower portion contacts the container containing flowable product delivered to said analysis position by said conveyor means.

5. An apparatus for analyzing a flowable product in accordance with claim 4, wherein said conveyor means delivers a container containing flowable product to said analysis position in a first direction, said apparatus further comprising a first container moving means positioned proximal said analysis position, said first container moving means constructed to move a container containing flowable product in said analysis position in a second direction, said second direction being opposite said first direction, said first container moving means constructed to move a container containing flowable product to a position spaced from said ultrasound transducer assembly.

6. An apparatus for analyzing a flowable product in accordance with claim 5, wherein said first container moving means comprises a piston.

7. An apparatus for analyzing a flowable product in accordance with claim 5, wherein said first container moving means comprises a robot.

8. An apparatus for analyzing a flowable product in accordance with claim 4, wherein said conveyor means comprises a conveyor belt.

9. An apparatus for analyzing a flowable product in accordance with claim 4, wherein said conveyor means comprises an agitator.

10. An apparatus for analyzing a flowable product in accordance with claim 4, wherein said conveyor means comprises a robot constructed to transport a container containing flowable product to said analysis position.

11. An apparatus for analyzing a flowable product in accordance with claim 4, wherein said conveyor means comprises a robot constructed to agitate a flowable product in a container.

12. An apparatus for analyzing a flowable product in accordance with claim 4, wherein said apparatus further comprises a second container moving means positioned proximal said analysis position, said second container moving means constructed to move a container containing flowable product out of contact with said conveyor means.

13. An apparatus for analyzing a flowable product in accordance with claim 12, wherein said second container moving means comprises a piston.

14. An apparatus for analyzing a flowable product in accordance with claim 12, wherein said second container moving means comprises a robot.

15. An apparatus for analyzing a flowable product in accordance with claim 4, said apparatus further comprising a processing unit coupled to said ultrasound transducer assembly, said processing unit constructed to analyze ultrasonic wave patterns received by said ultrasound transducer assembly from a container containing flowable liquid.

16. A method for analyzing a flowable product, said method comprising the steps of:

providing a container containing flowable product;

providing an agitator for agitating said container containing flowable product;

providing a conveyor assembly for conveying said container containing flowable product from said agitator to an analysis position;

providing an ultrasound transmissive pad assembly comprising a pad defining a chamber therein and further comprising an ultrasound transducer, a liquid acoustical couplant contained in said chamber defined by said pad, said ultrasound transducer being in ultrasonic contact with said liquid acoustical couplant, said pad having an upper portion and a lower portion;

positioning said ultrasound transmissive pad assembly proximal said analysis position such that said pad is in physical contact with said container containing flowable product when said unit of said container containing flowable product is in said analysis position, said ultrasound transmissive pad assembly positioned such that said upper portion of said pad contacts said unit of liquid product before said lower portion of said pad contacts said unit of liquid product;

providing a processing unit for analyzing ultrasound wave patterns received by said ultrasound transmissive pad assembly;

placing said container containing flowable product in said agitator;

agitating said container containing flowable product using said agitator;

delivering said container containing flowable product from said agitator to said analysis position using said conveyor assembly;

ultrasonically analyzing said container containing flowable product using said ultrasound transmissive pad assembly; and analyzing an ultrasound wave pattern received by said ultrasound transmissive pad assembly using said processing unit.

17. A method in accordance with claim 16, wherein said method further includes the steps of:

providing a first piston constructed to move said container containing flowable product in said analysis position away from said ultrasound transmissive pad assembly;

providing a second piston constructed to move said container containing flowable product off of said conveyor assembly;

placing said first and second pistons in positions proximal said analysis position;

activating said first piston after ultrasonically analyzing said unit of liquid product using said ultrasound transmissive pad assembly, whereby said unit of liquid product is moved away from said ultrasound transmissive pad assembly; and activating said second piston after said first piston has been activated, whereby said unit of liquid product is moved off of said conveyor assembly by said second piston assembly.

\* \* \* \* \*